United States Patent [19]
Strickler et al.

[11] Patent Number: 6,160,187
[45] Date of Patent: Dec. 12, 2000

[54] METHOD FOR MAKING GLYCOL IN AN ADIABATIC REACTOR SYSTEM

[75] Inventors: Gary R. Strickler; Von G. Landon; Guo-shuh John Lee, all of Midland; William J. Rievert, Beaverton, all of Mich.

[73] Assignee: The Dow Chemical Company, Midland, Mich.

[21] Appl. No.: 09/207,724

[22] Filed: Dec. 8, 1998

Related U.S. Application Data

[60] Provisional application No. 60/069,972, Dec. 18, 1997, and provisional application No. 60/089,188, Jun. 12, 1998.

[51] Int. Cl.[7] .................................................. C07C 27/00
[52] U.S. Cl. .............................................................. 568/867
[58] Field of Search ............................................. 562/867

[56] References Cited

U.S. PATENT DOCUMENTS 4,701,571  10/1987  Soo et al. .

*Primary Examiner*—Paul J. Killos
*Attorney, Agent, or Firm*—Elisabeth T. Jozwiak; John B. Treangen

[57] ABSTRACT

A method for making glycol in an adiabatic reactor system including feeding water and an epoxide into at least one adiabatic reactor under conditions such that epoxide and the water react to form a glycol product stream. The adiabatic reactor contains a catalyst bed which undergoes swelling during its useful lifetime, and the adiabatic reactor operates under conditions sufficient to reduce the rate of catalyst swelling relative to a non-adiabatic reactor system. Other aspects of the invention include the combination of splitting the feed between multiple adiabatic reactors in combination with the cross exchange of heat between feeds and products with heat exchangers, such that an energy efficient process that provides long catalyst stability and minimal catalyst swelling results.

17 Claims, 3 Drawing Sheets

(COMPARATIVE)

(COMPARATIVE)

METHOD FOR MAKING GLYCOL IN AN ADIABATIC REACTOR SYSTEM

This application claims the benefit of U.S. Provisional Application No. 60/069,972, filed Dec. 18, 1997 (incorporated herein by reference) and U.S. Provisional Application No. 60/089,188, filed Jun. 12, 1998 (incorporated herein by reference).

BACKGROUND OF THE INVENTION

This invention relates to a method for making glycols, preferably ethylene glycol, from alkylene oxide and water.

Alkylene glycols, such as ethylene glycol and propylene glycol, are widely used as raw materials in the production of polyesters, polyethers, antifreeze, solution surfactants, and as solvents and base materials in the production of polyethylene terephthalates (e.g. for fibers or bottles). Commercial processes for the preparation of alkylene glycols typically involve the liquid phase hydration of the corresponding epoxide in the presence of a large molar excess of water (see, e.g., Kirk-Othmer, *Encyclopedia of Chemical Technology*, Vol. 11, Third Edition, page 929 (1980)). When epoxides react with water to form monoglycols or with the hydroxyls on the monoglycols to form diglycols, a large amount of energy is released (about 20 kcal/mole of epoxide). If not removed from the reaction system, this energy causes the reaction medium's temperature to increase significantly. In some processes, it is imperative that the reaction energy be removed, while in others it is desired to allow the reactants to absorb the energy and heat up.

Typically, the reaction is carried out in two different types of commercial reactor practices. In one method, adiabatic operation, no heat is removed from the reactor. The temperature rise is controlled by feeding a large excess of water to allow the heat to be absorbed by the water feed. The adiabatic reactor is usually a cylindrical vessel or series of vessels with no heat transfer between vessels, operated in plug flow manner to obtain maximum monoglycol selectivity. In a second method, nonadiabatic operation, heat is removed from the reactor by transferring it to a coolant as the reaction proceeds. Here the combined feed of water and epoxide is fed to a heat exchange reactor and the heat is immediately removed by the heat exchanger as it forms. With appropriate controls and reactor design, nearly isothermal conditions can be maintained and the reaction product leaves at about the same temperature as the feed because the heat of reaction is removed by the coolant. This type of reactor is most often a shell-and-tube heat exchanger used as a reactor (referred to as a tubular, multitubular, isothermal, or heat exchange reactor), where the reaction mixture passes through several long narrow tubes, and a coolant passes on the outside of the tubes. This type of reactor is generally operated in plug flow manner to obtain maximum monoglycol selectivity.

The primary byproducts of hydrolysis reactions are di-, tri-, and higher glycols. However, as compared to monoalkylene glycols, the demand for di-, tri-, tetra-, and polyalkylene glycols is low. The formation of the polyglycols is due to the reaction of the epoxide with alkylene glycols. As epoxides are generally more reactive with glycols than they are with water, the aforementioned two commercial reactor types generally require an even greater excess of water in order to favor a commercially attractive selectivity to the monoglycol product. For example, a typical commercially practiced method for making ethylene glycol has a molar selectivity to monoethylene glycol (MEG) of about 88% at a water to ethylene oxide (EO) mass feed ratio of 8:1, about 20 times the stoichiometric amount of water required for complete reaction. Selectivity is calculated by dividing the number of moles of EO consumed to form a given product divided by the total number of moles of EO converted to all products. However, even in light of such large excesses of water, it would be desirable for the selectivity to the monoalkylene glycols to be even higher. In addition, increasing the water to epoxide feed ratio also increases the cost of distilling water from the glycol. Thus, there is much interest in alternative processes that increase monoalkylene glycol selectivity without increasing production costs.

A number of publications show that higher selectivity to monoalkylene glycols can be achieved if the reactions are conducted using heterogeneous catalytic processes, such as with anion exchange resin catalysts. See, for example: EP-A-156,449 (metalate-containing anion exchange resins); JP-A-57-139026 (anion-exchange resin in the halogen form); Russian Patent Nos. 2002726 and 2001901 (anion exchange resin in the bicarbonate form); WO/20559A (anion exchange resin); WO 97/33850 (anion exchange resin); and co-pending U.S. Provisional Patent Application No. 60/069,972, filed Dec. 18, 1997. U.S. Pat. Nos. 4,701,571 and 4,982,021 disclose various possible reactor configurations for the production of alkylene glycols using metalate anion exchange resin catalyst, and these references also suggest that isothermal reactors may be preferred because the amount of catalyst required may be less than that required in other types of reactor systems. Russian Patent No. 2001901 also discloses a method for catalytic production of alkylene glycols in a plug flow reactor or in a series of reactors with epoxide feed distributed to each reactor, where the reactors are 55–100% filled with bicarbonate-containing anion exchange resin catalyst, and the reactors are isothermal reactors.

Interestingly, none of the catalyst systems disclosed in the publications mentioned above have been successfully implemented for commercial production of alkylene glycols. The metalate-based resin system is not commercially attractive because metalate ions leach from the anion resin and contaminate the glycol product.

Moreover, anion exchange resin catalysts are believed to be compromised by limited tolerance to heat. As described in WO97/19043, monoglycol selectivity deterioration at high temperatures is the only reason why these catalysts have failed to achieve commercially viable prominence. Neither this reference or any of the aforementioned prior art mentions any problems associated with swelling of the catalyst resin.

It is known that the process of exchanging ions cause anion exchange resins to swell, as do the presence of solvents. See, for example: *Ion Exchangers*, K. Dorfner, Ed., (Walter de Gruyter: Berlin), 1991; and C. E. Harland, *Ion Exchange: Theory and Practice*, 2nd ed., (Royal Society of Chemistry: Cambridge), 1994. This type of swelling is reversible, and the extent of swelling is limited to no more than about 20% volume increase for ion exchange and about 100% for solvent swelling (based on a wet resin that is pre-swollen with water from its dry form), with no additional swelling even with prolonged exposure to the ions or solvent. The extent of this type of swelling depends on the type and concentration of the ions or solvent and on the type of resin matrix and extent of crosslinking. However, resin swelling under epoxide hydrolysis reaction conditions is different than swelling caused by solvents or ion exchange processes, yet, none of the above mentioned references teaches or suggests a mechanism for minimizing resin swelling during alkylene glycol production.

It is desirable to have a process for making alkylene glycols commercially, which minimizes and controls resin catalyst swelling and permits optimal temperature control for effective use of temperature-sensitive heterogeneous catalyst materials such as anion exchange resins.

SUMMARY OF THE INVENTION

In one aspect, the present invention is a method for making glycol in an adiabatic reactor system comprising feeding water and an epoxide into at least one adiabatic reactor under conditions such that epoxide and the water react to form a glycol product stream, the adiabatic reactor containing a catalyst bed which undergoes swelling during its useful lifetime, wherein the adiabatic reactor operates under conditions sufficient to reduce the rate of catalyst swelling relative to a non-adiabatic reactor system.

In a second aspect, the present invention is a method for making glycol in an adiabatic reactor system, comprising feeding water and an epoxide into a first adiabatic reactor under conditions such that the epoxide and the water react to form a glycol product stream comprising a glycol and water; removing the glycol product stream from the first adiabatic reactor and feeding it through at least one heat exchanger; and feeding the heat-exchanged glycol product stream through at least one more adiabatic reactor; wherein at least one of the adiabatic reactors comprises a catalyst bed, wherein each adiabatic reactor is in series and at least two of the adiabatic reactors are separated by at least one heat exchanger, and wherein temperature in the adiabatic reactor system is moderated by cross-exchanging the glycol product stream from at least one of the adiabatic reactors through a heat exchanger with at least one of the water, the epoxide feed, or a glycol product stream from a subsequent adiabatic reactor in series.

In a third aspect, the present invention is a method for making glycol in an adiabatic reactor system, comprising feeding water and an epoxide into a first adiabatic reactor under conditions such that the epoxide and the water react to form a glycol product stream comprising a glycol and water; removing the glycol product stream from the first adiabatic reactor; feeding the glycol product stream through at least one heat exchanger; and feeding the glycol product stream through at least one more adiabatic reactor; wherein each adiabatic reactor is in series and with the proviso that when one of the adiabatic reactors is a catalytic reactor and the next adiabatic reactor in series is a noncatalytic reactor, feeding the glycol product stream through at least one heat exchanger is optional when feeding the glycol product stream of the catalytic reactor to the noncatalytic reactor.

One advantage of the use of adiabatic reactor in the present invention includes minimization of continuous resin swelling under epoxide hydrolysis conditions. Such continuous and unlimited resin swelling can cause problems such as reactor plugging and reduction in catalyst efficiency. Another advantage of the present invention is that the use of adiabatic reactors allows for improvements in energy efficiency and temperature control.

By using adiabatic reaction, multiple reactors, catalytic beds, split epoxide feeds, and/or cross-exchange of heat, the method of this invention allows synthesis of glycols with efficient temperature control at attractive reaction rates while improving catalyst life by reducing swelling. It is only through the unique combination of splitting the feed between multiple adiabatic reactors in combination with the cross exchange of heat between feeds and products with intercoolers that an energy efficient process that provides long catalyst stability is created.

DETAILED DESCRIPTION OF THE INVENTION

This invention is a method for making glycols from epoxides and water. The preferred epoxides include ethylene oxide (EO), propylene oxide (PO), and butylene oxide (BO), and the preferred alkylene glycols include their respective monoalkylene glycols: ethylene glycol (EG), propylene glycol (PG), and butylene glycol (BG). Most preferably, this invention is a process for preparing monoethylene glycol from ethylene oxide and water.

Illustrations of various configurations of the adiabatic reactor systems are set forth in FIGS. 1–9. In FIGS. 1–9, the following reference numbers shall apply: 1 denotes a Water Feed; 2 denotes an Epoxide Feed; 3 denotes a Heated Water Feed (after being cross-exchanged); 4 denotes a Combined Water and Epoxide Feed; 5 denotes an Adiabatic Reactor; 6 denotes a Glycol Product Stream; 7 denotes a Heat Exchanger; 8 denotes a Cooled Glycol Product Stream (after being cross-exchanged); 9 denotes a Combined Glycol Product and Epoxide Feed; 10 denotes a Heated Glycol Product Stream (after being cross-exchanged); 11 denotes a Coolant-In Stream, entering Heat Exchanger 7; and 12 denotes a Coolant-Out Stream, exiting Heat Exchanger 7.

Figure 1:
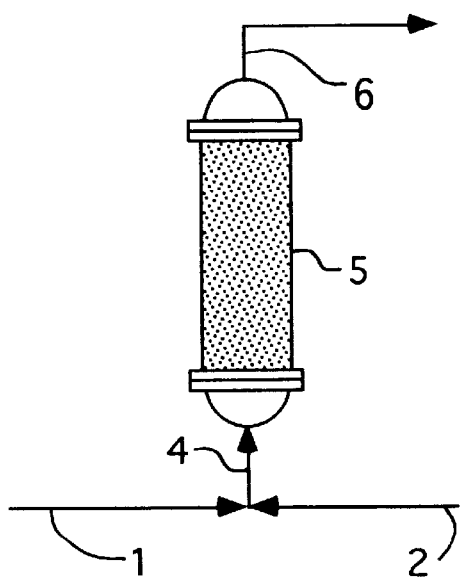
FIG. 1 is a schematic representation of the present invention, which illustrates a single catalytic adiabatic reactor.

FIG. 1 illustrates a single catalytic adiabatic reactor. Water Feed 1 is combined with Epoxide Feed 2 and fed to Adiabatic Reactor 5 as Combined Water and Epoxide Feed 4. The water and epoxide react in Adiabatic Reactor 5 to form Glycol Product Stream 6.

This reactor system offers the advantage of reduced resin swelling and unconstrained resin expansion versus other types of reactors. Versus a noncatalytic adiabatic reactor, the system depicted in FIG. 1 gives much higher selectivity at the same water to epoxide feed ratio.

By "adiabatic" it is meant that no substantial transfer of heat occurs to or from the reactor system. Thus, an adiabatic reactor system may include heat exchangers if they are used to cross-exchange heat in reactor feed and product streams, thereby conserving all of the heat in the reaction mixture, without transferring any heat to or from the surroundings, external process streams, or external equipment.

Surprisingly, compared to other reactor types, an adiabatic reactor has been found to reduce the rate of continuous swelling of anion exchange resin catalyst which occurs under epoxide hydrolysis reaction conditions. As mentioned above, it is known that ion exchange processes and solvents cause anion exchange resins to swell. This type of swelling is reversible, and the extent of swelling is limited. However, under conditions of alkylene oxide hydrolysis, especially EO hydrolysis, anion exchange resin catalyst unexpectedly swells continuously and irreversibly to an unlimited extent. Such continuous, unlimited swelling can create problems in an industrial situation, such as reactor plugging and a detrimental effect on selectivity.

Preferably, using the adiabatic reactor system of the present invention, the rate of continuous, unlimited swelling is reduced by at least 10% relative to non-adiabatic operation, more preferably at least about 20%, and even more preferably at least about 30%. Thus, for example, if the rate of continuous catalyst swelling is 1.0% per day using non-adiabatic operation, then the rate of continuous swelling using the adiabatic reactor system of the present invention is preferably reduced to 0.9% or less per day.

Of course, the rate of catalyst swelling will depend upon the specific catalyst. Moreover, more swelling can be tolerated with a catalyst having a higher activity. Preferably the rate of catalyst swelling is reduced to less than 1 % per day, more preferably less than 0.9% per day, and even more preferably less than 0.8% per day.

Continuous, unlimited catalyst swelling has been discovered to be caused by a combination of high EO concentrations and high temperatures, which accelerates epoxide polymerization in anion exchange resins. Thus, if the EO concentration and/or the reactor temperature can be lowered, the swelling problem can be reduced. In the adiabatic reactors of the present invention, the inlet side of the reactor has relatively high EO concentration, but the temperature is lower than could be achieved in a non-adiabatic or isothermal reactor, which will help reduce resin swelling. Likewise, at the outlet side of the adiabatic reactor, the temperature is higher, but the EO concentration is lower and thus will result in reduced resin swelling.

Multitubular or so-called isothermal reactors are inappropriate for use with anion exchange resin catalysts because the tubes in the reactors are long and narrow. The weight of the resin and the friction of the expanding resin against the tube wall prevent the resin from freely expanding along the length of the tube, plugging off flow through the catalyst bed.

The adiabatic reactor must allow unconstrained expansion of the resin catalyst; otherwise, the resin will expand against the walls of the reactor, plugging off flow through the catalyst bed and generating very high pressures which could rupture the reactor. This requires that the reactor volume be greater than the initial volume of the resin bed and that the shape and/or proportions of the reactor and/or catalyst bed be such that the resin can expand freely into the portion of the reactor that does not initially contain catalyst, without binding or bridging against the reactor walls.

These requirements can be met by using, for example, a vertical cylindrical vessel for the adiabatic reactor, with a sufficiently low height to diameter ratio of the catalyst bed. In such a reactor, the catalyst could be located at the bottom portion of the vessel and allowed to expand upward over time. Preferably, the height to width ratio of the catalyst bed in the adiabatic reactor is less than or equal to about 20:1, more preferably less than or equal to about 15:1, and even more preferably less than or equal to about 10:1. Preferably, the height to width ratio of the catalyst bed in the adiabatic reactor is at least about 0.1:1, more preferably at least about 0.5:1, and even more preferably at least about 1:1.

A catalyst bed height to width ratio greater than about 20:1 results in a system which does not allow the resin to expand freely. Because the resin expands continuously as a function of time under reaction conditions, the initial height to width ratio should be such that the final height to width ratio does not exceed about 20:1. For example, if the resin is expected to double in volume over the life of the catalyst, the bed should have a height to diameter ratio no higher than about 10:1, and the reactor must have a height to diameter ratio of at least 20:1.

Another type of adiabatic reactor configuration that allows for unconstrained resin swelling is a vessel with one or more conical shaped sections, where the reactor diameter increases continuously from the bottom to the top of a conical section, and the angle of inclination of a conical section is such that the resin can expand upward freely by minimizing friction and lateral forces against the reactor wall. The reactor may have short cylindrical sections at the inlet and outlet and also between conical sections, if there is more than one conical section. The angle of inclination of a conical section necessary to allow the resin to expand freely is determined by the properties of the catalyst bed. Preferably, the angle of inclination is at least 1 degree from vertical, more preferably at least about 5 degrees from vertical, and even more preferably at least about 10 degrees from vertical. Preferably the angle of inclination is less than or equal to about 45 degrees from vertical, more preferably less than or equal to about 35 degrees from vertical, and even more preferably less than or equal to about 30 degrees from vertical. Other than for economical considerations, this reactor configuration has no upper limit on the ratio of height to width, as there is for a vertical cylindrical vessel.

Yet another type of reaction vessel is a combination of cylindrical shaped sections having increasing diameter from bottom to top. In this manner, a small diameter cylindrically shaped lower section is connected to one or more cylindrically shaped sections of increasing diameter, such that the diameter increases discretely from the bottom to the top of the vessel.

The cylindrical and conical reactor configurations mentioned above are only examples of adiabatic reactors that allow unconstrained resin expansion, and the invention is not limited to those configurations. Other configurations are possible that meet the requirements for unconstrained resin expansion.

Preferably, the reaction mixture is fed to the top of the adiabatic reactor. The reaction mixture then flows downward through the catalyst bed, where it reacts and forms glycol product, then immediately exits the reactor. Downflow operation offers advantages over upflow operation for some systems. For example, in downflow operation, noncatalyzed reactions that may occur above the catalyst bed (i.e., in the section of the reactor designed to accommodate resin expansion) are minimized because the inlet temperature is at a minimum, and any reaction that does occur will likely not cause significant loss of monoglycol selectivity because water concentration is at a maximum. Moreover, downflow operation avoids fluidization of the catalyst bed, which can occur in upflow operation at sufficiently high velocities of the reaction mixture. Fluidization could lead to catalyst attrition and reduce monoglycol selectivity due to axial mixing and more noncatalytic reaction in the higher void volume often associated with a fluidized bed.

Figure 2:
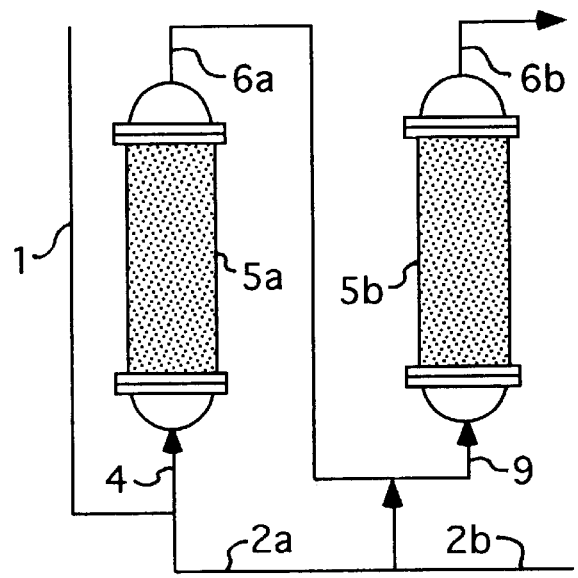
FIG. 2 is a schematic representation of the present invention, which illustrates two catalytic adiabatic reactors with no heat exchanger between them.

FIG. 2 illustrates a reactor system which includes two catalytic adiabatic reactors in series with no heat exchanger. Epoxide Feed 2 is split into streams 2a and 2b. Water Feed 1 is combined with Epoxide Feed 2a and fed to Adiabatic Reactor 5a as a Combined Water and Epoxide Feed 4. The water and epoxide react in Adiabatic Reactor 5a to form Glycol Product Stream 6a. Stream 6a is combined with Epoxide Feed 2b and fed as Combined Glycol Product and Epoxide Feed Stream 9 to Adiabatic Reactor 5b, where further reaction occurs to produce Glycol Product Stream 6b.

An advantage of the configuration in FIG. 2 is realized for systems where the catalyst swelling rate is a strong function of epoxide concentration. The epoxide feed is split and fed to each reactor separately. In this manner, the amount of reaction and temperature rise can be controlled in both reactors, and the epoxide concentration is lower than in a single adiabatic reactor. Because monoalkylene glycol selectivity in catalytic reactors is higher than in noncatalytic reactors, this system is optimal if maximum selectivity is desired.

Figure 3:
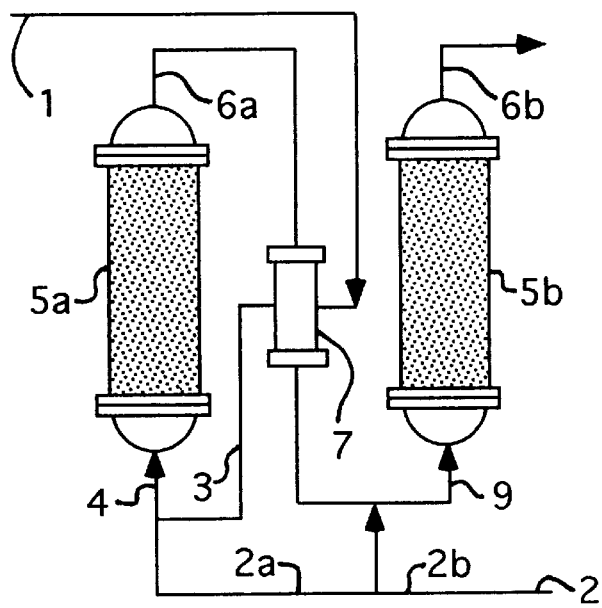
FIG. 3 is a schematic representation of the present invention, illustrating two catalytic adiabatic reactors in series with one heat exchanger between them.

Yet another aspect of the present invention includes an adiabatic reactor system comprising at least two adiabatic reactors in series, wherein each adiabatic reactor is separated by at least one heat exchanger. Such a system is illustrated in FIG. 3, which depicts two catalytic adiabatic reactors with a heat exchanger between them. Water Feed 1 is fed to Heat Exchanger 7 where it is heated with Glycol Product Stream 6a from the first Adiabatic Reactor 5a. Epoxide Feed 2 is divided into two feed streams. Heated Water Feed Stream 3 is combined with the Epoxide Feed 2a and fed to the first Adiabatic Reactor 5a as Combined Water and Epoxide Feed 4. The water and epoxide react in the first Adiabatic Reactor 5a to form Glycol Product Stream 6a. Stream 6a exits the reactor and is fed to Heat Exchanger 7 where it is cooled by cross-exchanging with Water Feed 1. The Cooled Glycol Product Stream 8 is then combined with Epoxide Feed 2b and fed as stream 9 to the second Adiabatic Reactor 5b, where further reaction occurs to produce the Glycol Product Stream 6b.

A particular advantage of the configuration in FIG. 3 is realized for systems with high feed ratios of water to epoxide, where low reaction temperatures and high monoalkylene glycol selectivity are required. The epoxide feed is split and fed to each reactor separately. In this manner, the amount of reaction and temperature rise can be controlled in both reactors. Because monoalkylene glycol selectivity in catalytic reactors is higher than in noncatalytic reactors, this system is optimal if maximum selectivity is desired. Versus a noncatalytic adiabatic reactor, this system gives much higher selectivity at the same water to epoxide feed ratio. Versus a single catalytic adiabatic reactor, this system provides an environment that will result in lower rates of catalyst swelling due to lower epoxide concentration in the feed. Versus a system with two catalytic adiabatic reactors with split epoxide feed but no heat exchanger, this system requires much less catalyst because the reaction occurs at a higher average temperature, where the reaction rate is higher, while staying below the catalyst degradation temperature. In addition to utilizing adiabatic reactors, the whole reaction system is adiabatic and does not require external cooling. This allows the heat of reaction to be left in the product stream and results in energy efficiency.

For the present invention, at least one of the adiabatic reactors in series must contain a catalyst bed comprising a heterogeneous catalyst. If one of the adiabatic reactors contains a catalyst bed ("catalytic reactor"), and it is followed in series by an adiabatic reactor that does not contain a catalyst bed ("noncatalytic reactor"), another embodiment of this invention is, optionally, to not have a heat exchanger separating the catalytic reactor and the noncatalytic reactor.

The temperature control utilized in the present invention has several advantages over the prior art. For example, by cross-exchanging various process streams, the present invention incorporates energy efficiency by transferring the heat of reaction to the feed, which can result in an adiabatic reaction system that eliminates the need to provide any external cooling. By cooling product streams with the initial feed streams, inlet stream temperatures to subsequent reactors are lowered. Such lower inlet stream temperatures are desirable for sustaining longer catalyst life and, as described above, for reducing resin swelling.

In addition, it is noted that when the reactors do not contain catalyst, using a heat exchanger and operating the system with a split epoxide feed results in a reactor system that requires more reactor volume when compared to a single adiabatic reactor system. Surprisingly, it was discovered that for systems where catalysts are employed, the use of two and three reactor systems equipped with heat exchangers and employing a split feed technique requires less catalyst than a comparable single adiabatic catalytic reactor system. This improvement in productivity reduces catalyst requirements and improves the economics of the present invention. Furthermore, by using multiple reactors rather than a single reactor, the epoxide feed can be split amongst the reactors such that the epoxide concentration at the inlet of each reactor is lower than would be in a single reactor, helping to further reduce resin swelling.

Figure 4:
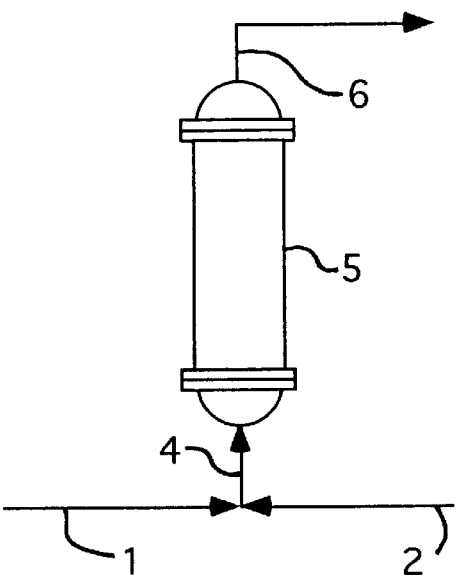
FIG. 4 is a schematic representation of a comparative embodiment, which illustrates a single noncatalytic adiabatic reactor.

FIG. 4 is for comparative purposes only and is not an embodiment of this invention. It illustrates a single noncatalytic adiabatic reactor. The configuration is identical to that in FIG. 1, except that the reactor does not contain catalyst.

Figure 5:
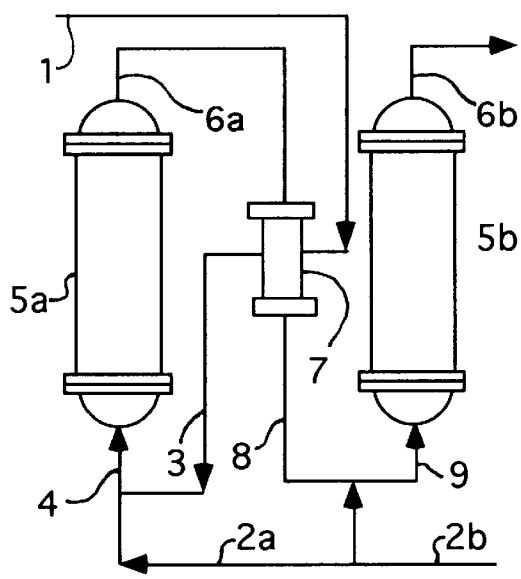
FIG. 5 is a schematic representation of a comparative embodiment, illustrating two noncatalytic adiabatic reactors in series with one heat exchanger between them.

FIG. 5 is for comparative purposes only and is not an embodiment of this invention. It illustrates two noncatalytic adiabatic reactors with a heat exchanger between them. The configuration is identical to that in FIG. 3, except that the reactors do not contain catalyst. Unlike the catalytic reactor systems shown in FIGS. 1 and 3, this system does not result in smaller reactor volumes when compared with a single noncatalytic adiabatic reactor.

Figure 6:
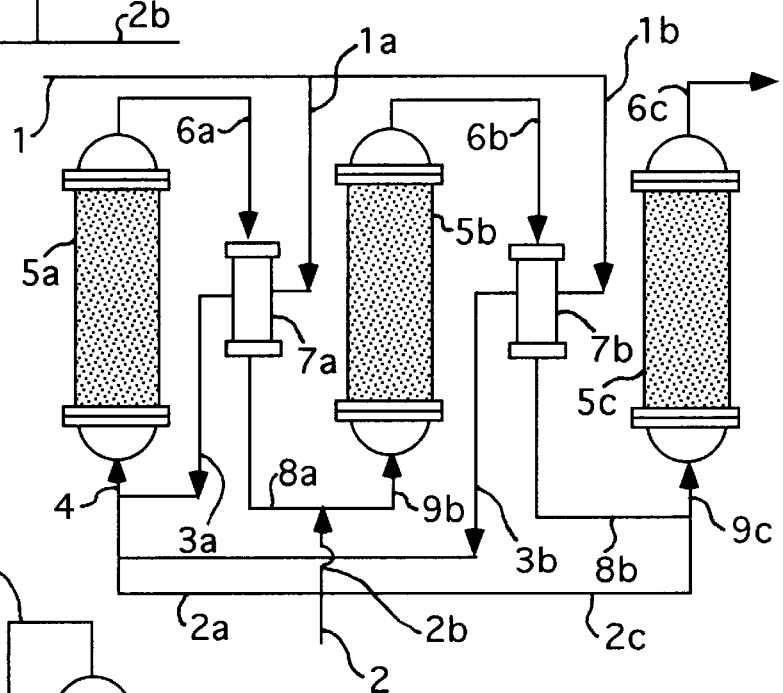
FIG. 6 is a schematic representation of the present invention, illustrating three catalytic adiabatic reactors in series with one heat exchanger between each of them.

In FIG. 6, three catalytic reactors are employed. Water Feed 1 is split into streams 1a and 1b. Epoxide Feed 2 is split into streams 2a, 2b, and 2c. Water Feed 1a is fed to Heat Exchanger 7a where it is heated with Glycol Product Stream 6a from the first Adiabatic Reactor 5a to form the Heated Water Feed 3a. Heated Water Feed 3a is combined with Heated Water Stream 3b from Heat Exchanger 7b. Heated Water Feeds 3a and 3b are combined with Epoxide Feed 2a to form Combined Water and Epoxide Stream 4. Stream 4 is fed into the first Adiabatic Reactor 5a to react and form Glycol Product Stream 6a, which exits the reactor and is cooled in the first Heat Exchanger 7a. Cooled Glycol Product Stream 8a is combined with Epoxide Feed 2b to form Combined Glycol Product and Epoxide Feed 9b. Stream 9b is fed to the second Adiabatic Reactor 5b to react and form Glycol Product Stream 6b, which exits the reactor and is cooled in the second Heat Exchanger 7b. Cooled Glycol Product Stream 8b is combined with Epoxide Feed 2c to form Combined Glycol Product and Epoxide Feed 9c and fed into a third Adiabatic Reactor 5c, where further reaction occurs to produce Glycol Product Stream 6c.

The advantage of the configuration shown in FIG. 6 is realized for systems where higher initial reaction temperatures are required or where lower water/epoxide feed ratios are desired. By using three reactors, a higher inlet temperature can be achieved without a consequential increase in the maximum temperature by spreading the total adiabatic temperature rise over three reactors. The epoxide feed is split and fed to each reactor separately. In this manner, the amount of reaction and temperature rise can be controlled in all three reactors. Versus a noncatalytic adiabatic reactor, this system gives much higher selectivity at the same water to epoxide feed ratio. Versus a single catalytic adiabatic reactor, this system requires much less catalyst because the reaction occurs at a higher average temperature while staying below the catalyst degradation temperature. Versus a system with two catalytic adiabatic reactors with a heat exchanger, this system requires slightly less catalyst at the same water to epoxide feed ratio and also allows operation at a lower water to epoxide feed ratio, which results in a higher concentration of glycol in the product. This reduces the amount of water that must be removed from the product stream, which saves energy and reduces the size of the evaporators. The system shown in FIG. 6 also reduces the rate of continuous unlimited catalyst swelling.

Figure 7:
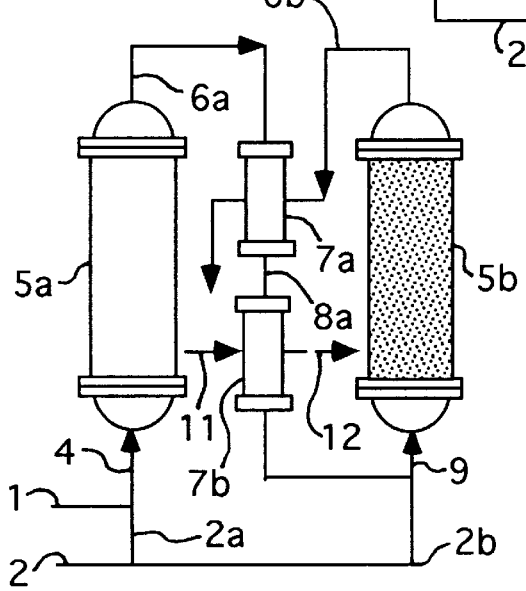
FIG. 7 is a schematic representation of the present invention, illustrating two adiabatic reactors with two heat exchangers between them, the first reactor being a noncatalytic reactor, the second reactor being a catalytic reactor.

FIG. 7 shows a system with two reactors and two heat exchangers. The first Adiabatic Reactor 5a is a noncatalytic reactor and the second Adiabatic Reactor 5b is a catalytic reactor. In this system, the catalytic Adiabatic Reactor 5b is used as a finishing reactor. Due to temperature constraints on the catalyst and low noncatalytic reaction rates, the noncatalytic Adiabatic Reactor 5a is operated at a higher temperature than the catalytic Adiabatic Reactor 5b. The Heat Exchangers (7a and 7b) are arranged for maximum energy efficiency.

More specifically for FIG. 7, Epoxide Feed 2 is split and fed to each reactor separately as streams 2a and 2b. Preheated Water Feed 1 is combined with Epoxide Feed 2a to form Combined Water and Epoxide Stream 4, which is fed to the noncatalytic Adiabatic Reactor 5a to react and form Glycol Product Stream 6a. Stream 6a is cooled in Heat Exchanger 7a by cross-exchanging with Glycol Product Stream 6b from the catalytic Adiabatic Reactor 5b. Cooled Glycol Product Stream 8a from Heat Exchanger 7a is further cooled in Heat Exchanger 7b by cross-exchanging with a coolant which enters Heat Exchanger 7b as Coolant-In Stream 11 and exits as Coolant-Out Stream 12. Cooled Glycol Product Stream 8b is combined with Epoxide Feed 2b to form Combined Glycol Product and Epoxide Feed 9. Stream 9 is fed to the catalytic Adiabatic Reactor 5b, where further reaction occurs to produce the Glycol Product Stream 6b. Stream 6b is heated in Heat Exchanger 7a to form Heated Glycol Product Stream 10.

The configuration shown in FIG. 7 is good for operation at low feed ratios of water to epoxide. Much of the epoxide is reacted in the noncatalytic reactor where glycol concentration is low, so there is little opportunity for selectivity loss to di- and triglycols. The balance of epoxide feed is reacted in the catalytic reactor using a monoglycol selective catalyst, thereby maintaining high selectivity. This configuration is particularly advantageous for expanding glycol production capacity of a facility with an existing noncatalytic reactor, while maintaining or decreasing the water feed rate to avoid additional equipment and energy for water evaporation. It is recognized that this system is not completely adiabatic due to the use of a separate coolant stream. However, it is more efficient than a system that does not use a heat exchanger for transferring heat between the products from the noncatalytic reactor to the products of the catalytic reactor. It also permits longer catalyst life through reduced swelling of the catalyst because the second reactor operates at lower epoxide feed ratios.

Figure 8:
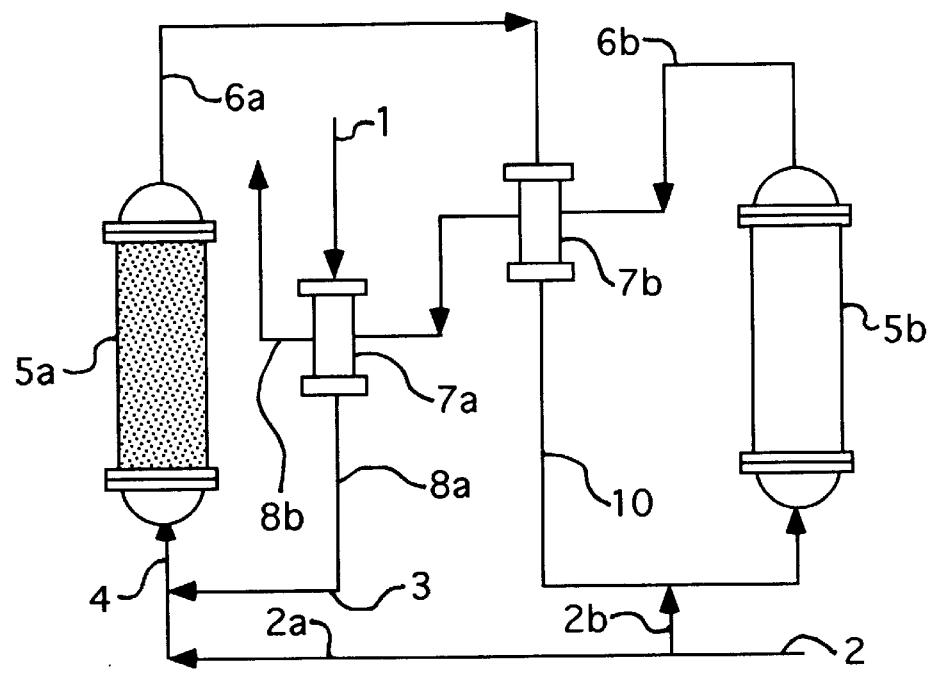
FIG. 8 is a schematic representation of the present invention, illustrating a first catalytic adiabatic reactor and a second noncatalytic adiabatic reactor, with a heat exchanger positioned before the first adiabatic reactor, and another heat exchanger positioned between the reactors.

FIG. 8 shows another system with two reactors and two heat exchangers. The first Adiabatic Reactor 5a is a catalytic reactor and the second Adiabatic Reactor 5b is a noncatalytic reactor. Epoxide Feed 2 is split into streams 2a and 2b. Water Feed 1 is preheated by cross-exchanging with Cooled Glycol Product Stream 8a in Heat Exchanger 7a. Heated Water Feed 3 is combined with Epoxide Feed 2a to form Combined Water and Epoxide Feed 4, which is fed to the catalytic Adiabatic Reactor 5a to form Glycol Product Stream 6a. Stream 6a is heated in Heat Exchanger 7b and exits as Heated Glycol Product Stream 10. Stream 10 is combined with Epoxide Feed 2b to form Combined Glycol Product and Epoxide Feed 9. Stream 9 which is fed into the second Adiabatic Reactor 5b to form Glycol Product Stream 6b.

The advantage of the configuration of FIG. 8 is realized for systems where a noncatalytic reactor already exists (as with a process retrofit), the feed is cooler than required for an exclusively noncatalytic reaction, selectivity is not critical, and energy savings are desired. The catalytic reactor is used to convert some of the epoxide at low temperatures, where the noncatalyzed reaction is very slow. The reaction is then completed at higher temperatures in the noncatalytic reactor. The epoxide feed is split and fed to each reactor separately, so that the amount of reaction and temperature rise can be controlled in the catalytic reactor to not exceed the degradation temperature of the catalyst. This reactor system does not provide selectivity as high as the systems shown in, for example, FIGS. 3 and 7, but it will provide selectivity higher than that obtained from a typical noncatalytic single adiabatic reactor system at the same water to epoxide feed ratio. It also allows for lower product discharge temperatures because the reaction can be commenced at lower temperature. This system will also allow economical operation for practitioners that wish to lower the water to epoxide feed ratios but wish to prevent product temperatures from becoming excessively high. It can also be used for retrofit applications where it is desired to improve product quality by lowering the maximum temperature for which the glycols are exposed. This configuration is particularly advantageous for expanding glycol production capacity of a facility with an existing noncatalytic reactor, while maintaining or decreasing the water feed rate to avoid additional equipment and energy for water evaporation. This system is completely adiabatic and offers energy savings.

Figure 9:
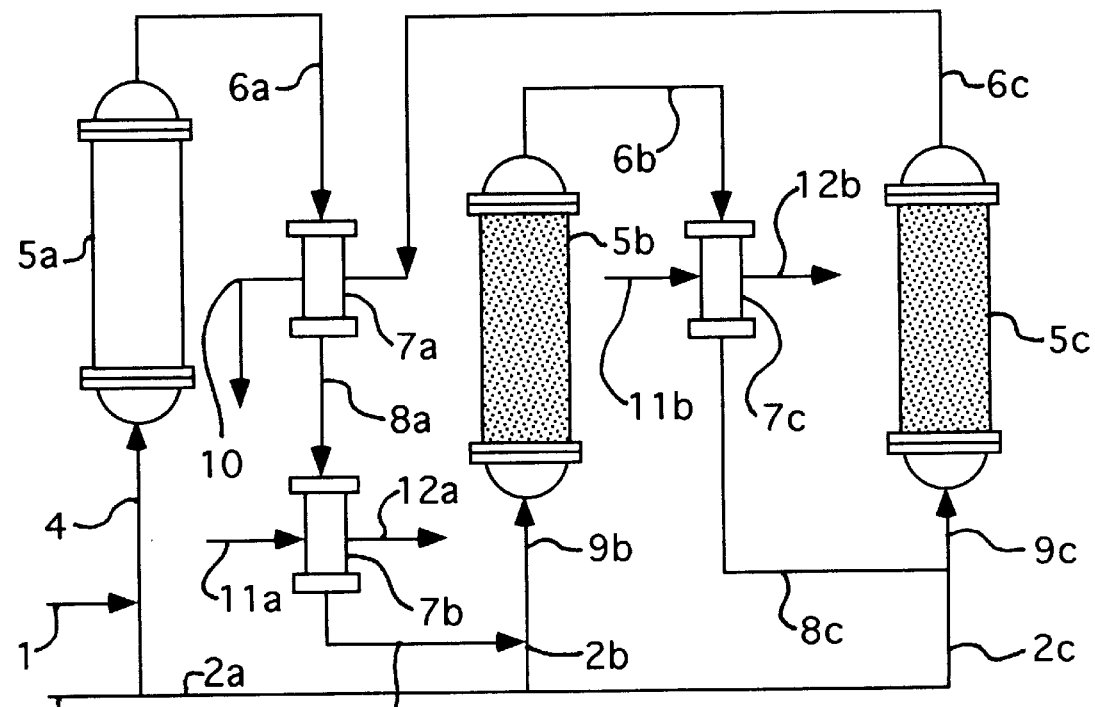
FIG. 9 is a schematic representation of the present invention, illustrating a first noncatalytic adiabatic reactor and a second catalytic adiabatic reactor with two heat exchangers between the first and second adiabatic reactors, and a third catalytic adiabatic reactor, with one heat exchanger between the second and third adiabatic reactors.

FIG. 9 illustrates three adiabatic reactors with two heat exchangers between the first and second adiabatic reactors and one heat exchanger between the second and third adiabatic reactors. The first reactor is noncatalytic, and the second and third reactors are catalytic. Epoxide Feed 2 is split into streams 2a, 2b, and 2c. The Water Feed 1 is combined with Epoxide Feed 2a to form Combined Water and Epoxide Stream 4. Stream 4 is fed into the noncatalytic Adiabatic Reactor 5a to react and form Glycol Product Stream 6a, which exits the reactor and is cooled in Heat Exchanger 7a by cross-exchanging with the Glycol Product Stream 6c. Cooled Glycol Product Stream 8a is further cooled in Heat Exchanger 7b by cross-exchanging with Coolant-In Stream 11a. Cooled Glycol Product Stream 8b is combined with Epoxide Feed 2b to form Combined Glycol Product and Epoxide Feed 9b, which is fed to the first catalytic Adiabatic Reactor 5b to make Glycol Product Stream 6b. Stream 6b is fed to Heat Exchanger 7c and cooled by cross-exchanging with a Coolant-In Stream 11b. Cooled Glycol Product Stream 8c is combined with Epoxide Feed 2c to form Combined Glycol Product and Epoxide Feed 9c, which is fed to the second catalytic Adiabatic Reactor 5c. Glycol Product Stream 6c is fed to Heat Exchanger 7a and cross-exchanged with Glycol Product Stream 6a and exits as Heated Glycol Product Stream 10.

The advantage of the configuration of FIG. 9 is realized for systems where a noncatalytic reactor exists and it is desired to increase the production capacity of the facility and obtain very high selectivity.

In light of the disclosure herein, those of skill in the art will recognize that many reactor system combinations and permutations of the claimed invention are possible. The configurations depicted in FIGS. 1–9 are for illustrative purposes only (with FIGS. 4 and 5 being for comparative purposes). It is essential, however, that the method of this invention utilize an adiabatic reactor system where at least one reactor contains catalyst.

For the practice of this invention, water of different purity may be used such as fresh water, deionized water, steam distilled water, condensate water (which may contain some residual glycol compounds), and also recycled water recovered from the dehydration process in the production of alkylene oxide and alkylene glycol (which may contain residual glycol). The water is provided in an amount which is in a stoichiometric excess of that required for forming a desired glycol from reaction with epoxide. Preferably, the molar feed ratio of water to epoxide is at least about 1.1, more preferably at least about 2.0, and even more preferably at least about 5.0. Preferably, the molar feed ratio is no more than about 30, more preferably no more than about 25, and even more preferably no more than about 20. Those of skill in the art will recognize that this ratio will vary depending upon the epoxides employed, the reaction conditions, and the specific catalyst utilized.

The water and epoxide feed may be fed to the first adiabatic reactor separately or together as co-feed. The water and epoxide may be fed to the reactors as a gas, as a liquid, or as a combination thereof.

The first step of the method comprises feeding water and epoxide into a first adiabatic reactor under conditions such that the epoxide and the water react to form a glycol product stream comprising a glycol and water. For purposes of this invention, the "glycol product stream" shall be read broadly to include any product stream exiting the adiabatic reactor which contains at least glycol and water. For example, in a series of two or more reactors, after leaving the first adiabatic reactor it is likely that the glycol product stream will also contain unreacted epoxide. The glycol product is generally in mixture, solution, or contained within unreacted water.

In light of the disclosure herein, conditions which are conducive for the reaction to occur are within the skill in the art. Factors for consideration include the optimum temperature, pressure, and water to alkylene oxide ratio for reacting the feed stream(s) without providing conditions which significantly degrade the catalyst bed or selectivity to the desired product. For example, see co-pending U.S. Provisional Patent Application No. 60/069,972, filed Dec. 18, 1997, (previously incorporated herein by reference). The reaction temperatures in reactors containing typical catalyst beds are generally in the range of from about 30° C. to about 150° C., preferably from about 50° C. to about 120° C. The reaction temperatures in noncatalytic reactors are generally in the range of from about 100° C. to about 250° C., preferably from about 120° C. to about 200° C. The reaction pressures are generally in the range of about 100 kPa to about 10000 kPa, preferably 500 kPa to about 5000 kPa, with the intent of avoiding vapor formation.

As set forth hereinabove, a catalyst bed must be included in at least one of the adiabatic reactors in series. Typically the catalyst bed is a fixed catalyst bed, but it may be a fluidized bed, a moving bed, or a slurry. It is desirable to minimize the volume of liquid in the catalyst bed to reduce the required reactor volume and to minimize noncatalytic reactions which may lead to lower monoglycol selectivity. Thus, a fixed bed is preferred over other types of catalyst beds. The catalyst bed may comprise any material capable of catalyzing the desired reaction in the adiabatic reactor in which it is employed. It should be of such a nature as to allow reactants and products to pass through the bed, yet provide a sufficient surface area for catalytic contact. Desirably, the catalytic material is solid and is insoluble in either the reactants or the glycol products under the conditions in the process. For example, it may be a solid acid catalyst or a solid base catalyst or others such as catalytic metals and their oxides or halides suitable for a multitude of catalytic reactions and heterogeneous with the reaction or other components in the system.

Preferably, the catalyst for this invention is selected from the group consisting of aluminosilicate zeolites, amorphous aluminosilicates, solid acid catalysts, solid base catalysts, and anion exchange resins. More preferably, the catalyst for this invention is an anion exchange resin.

In light of the disclosure herein, selection of a suitable anion exchange resin is within the skill in the art. Preferable anion exchange resins, and methods for their use, are disclosed in co-pending U.S. Provisional Patent Application No. 60/069,972, filed Dec. 18, 1997 (previously incorporated herein by reference). Preferably, such anion exchange resins include the aforementioned halogenate, carbonate, and bicarbonate-type anionic exchange resins. Illustrative of halogenate-type exchange resins is the disclosure of JP-A-57-139026 (incorporated herein by reference). Illustrative of bicarbonate-type exchange resins are the disclosures of WO 95/20559, WO 97/33850, RU Patent Nos. 2002726 and 2001901 (each of which is incorporated herein by reference). It is particularly preferred that the anion exchange resin contain quaternary ammonium groups. Examples of suitable, commercially available, anion exchange resins include: Amberlite™ IRA 400 and 900 series (based on polystyrene resins, cross-linked with divinylbenzene) (Rohm and Haas); Lewatit™ M 500 WS (Bayer); Duolite™ A 368, A-101D, ES-131 and A-161 (Rohm and Haas); and DOWEX™ MSA-1, MARATHON A, and MARATHON MSA. Anion exchange resins with trimethyl benzyl ammonium groups (i.e., Type I resins) are particularly preferred for this invention.

In one embodiment of this invention, each subsequent adiabatic reactor in series contains a catalyst bed having higher catalytic activity than the previous reactor. This is particularly advantageous because it is observed that, in one embodiment of this invention, productivity to a desired monoglycol is highest in the first adiabatic reactor and progressively less in subsequent effects due to decreased concentration of reactants in each subsequent reactor. In order to increase the productivity in the subsequent reactors, catalyst beds are provided in sufficient activity to provide an acceptable selectivity to the desired glycols. To illustrate, in FIG. 2 the catalyst bed in the first Adiabatic Reactor 5a might contain a catalyst of low activity, but the catalyst bed in the second Adiabatic Reactor 5b would contain a catalyst of higher activity, and the catalyst bed in the third Adiabatic Reactor 5c would have the highest catalytic activity.

The reaction may also be conducted in the presence of carbon dioxide. Whether to provide carbon dioxide to the reaction may depend on whether a catalyst is utilized in the reactor and the type of catalyst used. For example, if an anion exchange resin is utilized as a catalyst, it may be desirable to provide an amount of carbon dioxide to the catalyst bed. The carbon dioxide may be provided to the reaction in any convenient manner. The carbon dioxide may, for instance, be introduced separately and/or with one or more of the feed streams. The carbon dioxide may be present in the reaction mixture in gaseous form or in the form of carbonic acid or in the form of salts of carbonic acid. Preferably, the carbon dioxide is present in the reaction mixture in an amount less than, or equal to, 0.1 wt %, preferably 0.05 wt %, more preferably 0.01 wt %. Most preferably the amount of carbon dioxide (or its equivalent such as $NaHCO_3$ or $Na_2CO_3$) present in the reaction mixture ranges from a lower level of 0.0001 wt %, more preferably 0.005 wt %, most preferably 0.001 wt %. "Weight percent of carbon dioxide", as used herein, is based upon the total weight of carbon dioxide in the reaction mixture in any form (e.g. dissolved $CO_2$, carbonic acid, carbonate, or bicarbonate). "Reaction mixture" is meant to include each of the components which are fed to the reaction system.

The reaction of this invention may also be conducted in the presence of a pH adjusting additive. Whether to provide a pH adjusting additive to the reaction may be driven by factors such as the type of catalyst used, and whether carbon dioxide is fed to the catalyst bed. For example, if the bicarbonate form of an anion exchange resin is utilized as a catalyst, it may be desirable to provide an amount of pH adjusting additive to the catalyst bed. Such additive typically comprises any organic or inorganic bases such as alkylamines, pyridine, alkali phosphates, alkali sulphates, alkali carbonates, alkali metal hydroxide, and combinations thereof. "Bases", as used herein, shall be defined as compounds that, when added to water, give a pH of greater than 7.0. Preferably, the pH adjusting additive comprises sodium hydroxide (NaOH). The pH adjusting additive is provided in an amount sufficient to maintain a pH of the reaction mixture at a lower limit of about 5.0, more preferably 5.5, and most preferably 6.0. For an upper pH limit, the pH adjusting additive is provided in an amount sufficient to maintain a pH of the reaction mixture below about 9.0, preferably 8.0, and more preferably 7.0. By referring to "pH of the reaction mixture" it is meant the pH of the mixture which includes each of the components which are fed to the reactor.

The invention will be further clarified by a consideration of the following examples, which are intended to be purely exemplary of the use of the invention.

EXAMPLES

Examples 1–3 were obtained by experiments with laboratory equipment. Examples 4–13 were generated using commercial simulation software available under the trade designation ASPEN PLUS (Aspen Technology, Inc., Cambridge, Mass.).

Example 1 (Comparative Example)

Preparation of the Catalyst

The catalyst was DOWEX MSA-1, chloride anion form, with a wet volumetric exchange capacity of 1.3 meq/ml. The chloride form of the resin was converted to the bicarbonate form for use in the example.

Description of the Reactor

The reactor was a jacketed, 1.1 cm inner diameter, 23 cm long, 316 Stainless Steel tube having a height to width ratio of 20.9:1. Heat transfer fluid was circulated through the jacket to maintain a constant, uniform reaction temperature, thereby creating isothermal conditions. A 3.2 mm outer diameter thermocouple with six evenly spaced junctions was mounted concentrically inside the tube to measure the reaction temperature. The tube was packed with 20 ml of the resin catalyst. Aqueous and ethylene oxide feed streams were pumped at constant flow rates, mixed and fed to the reactor. The reactor was operated at 12 bar to avoid vapor formation.

Feed Solution

The ethylene oxide feed was 99.9%, and the feed rate was 8.2 g/h. The aqueous feed was 64 g/h water saturated with 10% $CO_2$ in helium at 23° C. and 1 bar. The combined aqueous and EO feed had 0.014 wt % $CO_2$.

Results

The products were analyzed by gas chromatograph for ethylene oxide (EO), monoethylene glycol (MEG), diethylene glycol (DEG), and triethylene glycol (TEG). At the beginning of the experiment, the reactor temperature was 97° C., EO conversion was 80.1%, and EG selectivity was 98.4%. Molar selectivity is calculated by dividing the number of moles of EO consumed to form a given product divided by the total number of moles of EO converted to all products. After 27 days of operation, the reactor temperature was increased to 108° C. EO conversion immediately rose to 95% then continuously dropped to 86% after 42 more days of operation. At that point, the reactor temperature was raised to 117° C., and the conversion increased to 96% then continuously dropped to 80% after 37 more days of operation, when the reactor had to be shut down due to excessive pressure drop through the catalyst bed. It was discovered that the resin had expanded and completely filled the reactor, which caused the excessive pressure drop that led to shutting down the reactor. In fact, upon opening the reactor, some of the resin forced its way out of reactor to relieve the pressure that had built up due to swelling. The volume of the swollen resin was 40 ml, and the resin swelling rate was 1%/day.

This example was done under the conditions disclosed in Russian Patent Nos. 2002726 and 2001901 (i.e., bicarbonate form of anion exchange resin in the presence of $CO_2$).

Example 2 (Comparative Example)

The catalyst and reactor system were the same as in Example 1. The reactor temperature was maintained at 98±1° C. throughout the run.

Feed Solution

The ethylene oxide feed was 99.9% pure and the feed rate was 8.3 g/h. The aqueous feed was 64 g/h of deionized, $CO_2$-free water.

Results

At the beginning of the run, EO conversion was 95.7%, and EG selectivity was 98.8%. After 42 days of operation, the pressure drop became excessive and the reactor was shut down. The resin had expanded and completely filled the reactor, as in the previous example. The swollen resin volume was 35 ml. 20 ml of the swollen resin was reloaded into the reactor, and the experiment was continued. The EO conversion was 85% after reloading the reactor then dropped continuously over the next 101 days to 75%, when the pressure drop became excessive and the reactor was shut down again. The 20 ml of reloaded swollen resin had expanded further to 40 ml. The resin swelling rate was over 1.5%/day.

This example was done under the conditions disclosed in WO/20559A (i.e., bicarbonate form of anion exchange resin in the substantial absence of $CO_2$).

Example 3

The catalyst was the same as in Example 1.

Description of the Reactor

The apparatus illustrated in FIG. 1 was used. The reactor was an insulated, 2.4 cm inner diameter, 15.2 cm long, 316 Stainless Steel tube, having a height to width ratio of 6.3:1. A 3.2 mm outer diameter thermocouple with six evenly spaced junctions was mounted concentrically inside the tube to measure the reaction temperature. The tube was packed with 30 ml of the resin catalyst. Aqueous and ethylene oxide feed streams were pumped at constant flow rates, mixed, and fed to the top of the reactor. The reactor was operated at 12 bar to avoid vapor formation.

Feed solution

The ethylene oxide feed was 99.9% pure and the feed rate was 8.3 g/h. The aqueous feed was 64 g/h of deionized, $CO_2$-free water. The feed temperature was adjusted to maintain the temperature at 95° C. at a point inside the reactor that was 2.5 cm from the bottom (outlet) of the reactor.

Results

At the beginning of the experiment, EO conversion was 98.1%, and EG selectivity was 98.6%. The temperature in the reactor was 64° C. at the inlet and 104° C. at the outlet. The temperature rise was slightly less than adiabatic because there was a small amount of heat lost from the reactor. After 85 days of operation, the temperature in the reactor was 68° C. at the inlet and 98° C. at the outlet, EO conversion was 96.8%, EG selectivity was 98.6%, and the resin had expanded to 42.5 ml. There was no increase in pressure drop during the entire run. The resin expanded at a rate of less than 0.5%/day. This represents a reduction in catalyst swelling of 50% as compared to Example 1, and 67% as compared to Example 2.

Examples 4–13

The following examples were obtained by computer simulations, as described above. The simulations were done for manufacturing scale equipment with sufficient catalyst and reactor volume to obtain at least 99.9% epoxide conversion.

A second order kinetic model was developed for the catalyzed reactions mechanism using data obtained by feeding a reactor with different concentrations of ethylene oxide and water (5:1 to 15:1 by weight) and running at temperatures between 70° C. and 125° C. By combining these kinetics with previously measured kinetics for noncatalytic reactions, a comprehensive model was defined that predicts the rate of the reaction at each point in the adiabatic reactor system. The pre-exponential rate constants and activation energies for the reactions are shown in the table below wherein the following abbreviations apply: EO (ethylene oxide), EG (monoethylene glycol), DEG (diethylene glycol), and TEG (triethylene glycol).

TABLE 1

Reaction kinetics used for Examples 4–13

| Reactants | Product | Mechanism | Pre-exponential Factor (l/mol · s)* | Activation Energy (kcal/mol) |
|---|---|---|---|---|
| EO + $H_2O$ | EG | Catalytic | $1.60 \cdot 10^7$ | 18.9 |
| EO + EG | DEG | Catalytic | $1.63 \cdot 10^9$ | 23.3 |
| EO + DEG | TEG | Catalytic | $1.36 \cdot 10^6$ | 17.8 |
| EO + $H_2O$ | EG | Noncatalytic | $8.8 \cdot 10^5$ | 19.0 |
| EO + EG | DEG | Noncatalytic | $2.2 \cdot 10^6$ | 19.0 |
| EO + DEG | TEG | Noncatalytic | $2.2 \cdot 10^6$ | 19.0 |

*The reaction rate for the catalytic reactions is based on the gross or bulk volume of catalyst in a catalyst bed, whereas the reaction rate for noncatalytic reactions is based on the net liquid volume in the bed. Both types of reaction were accounted for in the catalyst bed, where about 40% of the volume is liquid.

Example 4

The apparatus depicted in FIG. 1 was used. EO (10° C. and 17.2 bar), at a rate of 17237 kg/h, is combined with 137892 kg/h of water (46° C. and 17.2 bar) and fed to a single adiabatic reactor 5 which contains a catalyst bed that is 5 meters in diameter by 11 meters in length. The product exiting the reactor is at 17.2 bar and 100° C. and contains 130890 kg/h water, 2.5 kg/h EO, 23970 kg/h EG, 263 kg/h DEG, and 2.5 kg/h TEG. The total volume of catalyst is 216 cubic meters. The EO conversion is 99.99%, and the EG selectivity is 98.7%.

Example 5

The apparatus shown in FIG. 2 was used. EO (10° C. and 17.2 bar), stream 2, is fed at a rate of 17237 kg/h to a splitter and equally divided into two feed streams, 2a and 2b. The first stream, 2a, is combined with 137892 kg/h of water (46° C. and 17.2 bar), stream 1, and fed to the first of two adiabatic reactors 5a which contains a catalyst bed that is 5.5 meters in diameter by 11 meters in length. The product from the first reactor reaches 69° C. The incompletely reacted material from the first reactor is then combined with the second EO stream and fed to the second reactor which contains a catalyst bed 3.25 meters in diameter by 10 meters in length. The product exiting the reactor is at 17.2 bar and 100° C. and contains 130893 kg/h water, 12 kg/h EO, 23957 kg/h EG, 263 kg/h DEG, and 2.5 kg/h TEG. The total volume of catalyst is 344 cubic meters. The EO conversion is 99.93% and the EG selectivity is 98.7%.

Example 6

The apparatus shown in FIG. 3 was used. EO (10° C. and 17.2 bar), stream 2, is fed to a splitter at a rate of 17237 kg/h and equally divided into two feed streams, 2a and 2b. Water (46° C. and 17.2 bar), stream 1, is fed at a rate of 137892 kg/h to the shell side of a heat exchanger, 7, where it is heated. The feed is combined with the first EO stream, 2a, and fed as a 68° C. mixture to the first of two adiabatic reactors, 5a, which contains a catalyst bed that is 2.75 meters in diameter by 10 meters in length. The product from the first reactor is cooled to 74° C. in heat exchanger 7 and then combined with the second EO stream 2b from the splitter. The combined material is then fed to the second reactor, which contains a catalyst bed 3.25 meters in diameter by 10 meters in length. The product exiting the reactor is at 17.2 bar and 101° C. and contains 130893 kg/h water, 3.5 kg/h EO, 23946 kg/h EG, 283 kg/h DEG, and 2.9 kg/h TEG. The total volume of catalyst is 143 cubic meters. The EO conversion is 99.98%, and the EG selectivity is 98.6%.

Example 7 (Comparative Example)

The apparatus shown in FIG. 4 was used. This is a comparative example only, because the reactor does not contain catalyst. EO (10° C. and 17.2 bar), at a rate of 17237 kg/h, is combined with 137892 kg/h of water (140° C. and 17.2 bar) and fed to a single noncatalytic adiabatic reactor 5. The reactor is 2 meters in diameter and 7 meters in length. The product exiting the reactor is at 17.2 bar and 182° C. and contains 131257 kg/h water, 3.4 kg/h EO, 21497 kg/h EG, 2238 kg/h DEG, and 134 kg/h TEG. The reactor volume is 22 cubic meters. The EO conversion is 99.98%, and the EG selectivity is 88.5%.

Example 8 (Comparative Example)

The apparatus shown in FIG. 5 was used. It is a comparative example only, because neither reactor contains catalyst. EO (10° C. and 17.2 bar), stream 2, is fed to a splitter at a rate of 17237 kg/h and equally divided into two feed streams, 2a and 2b. Water (140° C. and 17.2 bar), stream 1, is fed at a rate of 137892 kg/h and fed to the shell side of a heat exchanger 7 where it is heated. The feed is combined with the first EO stream 2a and fed as a 153° C. mixture to the first of two adiabatic reactors 5a which is 2 meters in diameter by 3 meters in length. The product from the first reactor is cooled to 162° C. in heat exchanger 7 and then combined with the second EO stream from the splitter. The combined material is then fed to the second reactor, which is 2 meters in diameter by 4.85 meters in length. The product exiting the second reactor is at 17.2 bar and 182° C., and contains 131257 kg/h water, 3.5 kg/h EO, 21495 kg/h EG, 2239 kg/h DEG, and 134 kg/h TEG. The total reactor volume is 24.6 cubic meters. The EO conversion is 99.98%, and the EG selectivity is 88.5%.

Example 9

The apparatus shown in FIG. 6 was used. EO (10° C. and 17.2 bar), stream 2, is fed to a splitter at a rate of 17237 kg/h and equally divided into three feed streams, 2a, 2b, and 2c. Water (46° C. and 17.2 bar), stream 1, is fed to a splitter at a rate of 137892 kg/h and divided into two equal feed streams, 1a and 1b. The first water stream, 1a, is sent to heat exchanger 7a where it is heated with product from reactor 5a. The second water stream 1b is fed to heat exchanger 7b where it is heated with the product from reactor 5b. The two water streams are then combined with the first EO stream 2a and fed to reactor 5a, which contains a catalyst bed 2 meters in diameter by 10 meters in length. The heated feed material is at 77° C. and 17 bar. The product from reactor 5a reaches 95° C. due to exothermic reaction, but it is cooled back to 80° C. by cross exchange with the first water feed 1a. The cooled material is then combined with the second EO stream and is fed to reactor 5b, which contains a catalyst bed 2 meters in diameter by 10 meters in length. The product stream from the second reactor reaches 97° C., but is cooled to 81° C. in exchanger 7b. The cooled material is combined with the third EO feed stream and fed to the third reactor which contains a catalyst bed 3 meters in diameter by 10 meters in length. The product, stream 6c, exiting the third reactor is at 17 bar and 101° C. and contains 130894 kg/h water, 0.7 kg/h EO, 23939 kg/h EG, 292 kg/h DEG, and 3.0 kg/h TEG. The total volume of catalyst is 133 cubic meters. The EO conversion is 99.99%, and the EG selectivity is 98.6%.

Example 10

The apparatus shown in FIG. 6 was used. The reactor configuration is the same as in the previous example, but the water to epoxide feed ratio is lower. EO (10° C. and 17.2 bar), stream 2, is fed to a splitter at a rate of 22680 kg/h and equally divided into three feed streams, 2a, 2b, and 2c. Water (28° C. and 17.2 bar), stream 1, is fed to a splitter at a rate of 137892 kg/h and divided into two equal feed streams, 1a and 1b. The first water stream 1a is sent to heat exchanger 7a where it is heated with product from reactor 5a. The second water stream 1b is fed to heat exchanger 7b where it is heated with the product from reactor 5b. The two water streams are then combined with the first EO stream 2a and fed to reactor 5a, which contains a catalyst bed 3 meters in diameter by 10 meters in length. The heated feed material is at 75° C. and 17 bar. The product from reactor 5a reaches 100° C. due to exothermic reaction, but it is cooled back to 78° C. by cross exchange with the first water feed 1a. The cooled material is then combined with the second EO stream and is fed to reactor 5b, which contains a catalyst bed 3 meters in diameter by 10 meters in length. The product stream from the second reactor reaches 101° C., but is cooled to 78° C. in heat exchanger 7b. The cooled material is combined with the third EO feed stream and fed to the third reactor which contains a catalyst bed 3 meters in diameter by 10 meters in length. The product stream 6c exiting the third reactor is at 17 bar and 100° C. and contains 128709 kg/h water, 13.1 kg/h EO, 31342 kg/h EG, 503 kg/h DEG, and 7.0 kg/h TEG. The total volume of catalyst is 212 cubic meters. The EO conversion is 99.95%, and the EG selectivity is 98.1%.

Example 11

The apparatus shown in FIG. 7 was used. EO (10° C. and 17.2 bar), stream 2, is fed to a splitter at a rate of 17237 kg/h and equally divided into two feed streams, 2a and 2b. Water (135° C. and 17.2 bar), stream 1, is fed at a rate of 137892 kg/h and combined with the first EO stream and fed to the noncatalytic adiabatic reactor, 5a, which is 2.5 meters in diameter by 10 meters in length. The product from the noncatalytic reactor is cooled to 110° C. in heat exchanger 7a. The material is then further cooled in heat exchanger 7b to 72° C. and then combined with the second EO stream from the splitter. The combined material is then fed to the second reactor, which contains a catalyst bed 3.25 meters in diameter by 10 meters in length. The product exiting the reactor is at 17.2 bar and 98° C. The product is then sent to the shell side of heat exchanger 7a where it is heated to 145° C. The product stream 10 contains 130992 kg/h water, 12.6 kg/h EO, 23292 kg/h EG, 802 kg/h DEG, and 30 kg/h TEG. The total volume of catalyst is 83 cubic meters. The EO conversion is 99.92%, and the EG selectivity is 96.0%.

Example 12

The apparatus shown in FIG. 8 was used. EO (10° C. and 17.2 bar), stream 2, is fed to a splitter at a rate of 17237 kg/h and equally divided into two feed streams, 2a and 2b. Water (46° C. and 17.2 bar), stream 1, is fed at a rate of 137892 kg/h, preheated in exchanger 7a to 72° C., and then combined with the first EO stream 2a. The combined stream 4 is fed to the catalytic adiabatic reactor 5a, which contains a catalyst bed 3.25 meters in diameter by 10 meters in length. The product 6a from the first reactor is combined with the second EO stream 2b from the splitter and preheated in exchanger 7b to 150° C. The combined material is then fed to the noncatalytic reactor 5b, which is 3.25 meters in diameter by 10 meters in length. The product exiting the reactor is at 17.2 bar and 176° C. The product is then sent to the tube side of heat exchanger 7b where it is cooled to 123° C. and then further cooled in exchanger 7a to 101° C. The product stream 8b contains 131166 kg/h water, 0.5 kg/h EO, 22093 kg/h EG, 1795 kg/h DEG and 74 kg/h TEG. The total volume of catalyst is 83 cubic meters. The EO conversion is 99.99%, and the EG selectivity is 91.0%.

Example 13

The apparatus shown in FIG. 9 was used. EO (10° C. and 17.2 bar), stream 2, is fed to a splitter at a rate of 17237 kg/h and divided into three feed streams, 2a, 2b, and 2c. The streams contain 4536, 6350, and 6350 kg/h of EO, respectively. Water (144° C. and 17.2 bar), stream 1, is fed at a rate of 137892 kg/h and combined with the first EO stream 2a and fed to the noncatalytic reactor 5a, which is 2.25 meters in diameter by 10 meters in length. The product from reactor 5a reaches 156° C. due to exothermic reaction, but it is cooled back to 120° C. by cross exchange with the product from reactor 5c. The product is further cooled in heat exchanger 7b to 80 ° C. The cooled material is then combined with the second EO stream 2b and is fed to reactor 5b, which contains a catalyst bed 3 meters in diameter by 7 meters in length. The product stream from the second reactor reaches 99° C., but is cooled to 82° C. in exchanger 7c. The cooled material is combined with the third EO feed stream 2c and fed to the third reactor 5c, which contains a catalyst bed 3 meters in diameter by 9 meters in length. The product stream 6c exiting the third reactor is at 17 bar and 101° C. and contains 130923 kg/h water, 5.0 kg/h EO, 23746 kg/h EG, 445 kg/h DEG, and 9.3 kg/h TEG. The total volume of catalyst is 113 cubic meters.

The EO conversion is 99.97%, and the EG selectivity is 97.8%.

the catalyst making the process economically viable, and to provide stable operation of the process.

Fluctuations in the feed temperature or composition can lead to undesirable transient exotherms in the first adiabatic reactor. These can be minimized by bypassing feed around the heat exchanger between the reactors, by sending part of the feed to the second reactor, or by adding water to the feed. Feeding additional $CO_2$ typically is not helpful with these types of upsets because it takes the catalyst a long time to respond to the effect of changing $CO_2$ concentration in the feed.

As the catalyst deactivates, several steps can be taken to compensate for the loss of activity, thereby lengthening the useful lifetime of the catalyst. These steps include, in the preferred sequence: (1) Decreasing the amount of $CO_2$ added to the feed; (2) reducing the amount of feed that bypasses the heat exchanger between the reactors; and (3) preheating the feed in an additional heat exchanger. Step 2 will increase the average reaction temperature of the first reactor. Step 3 will increase the average reaction temperature of both reactors. The hot stream used to preheat the feed in Step 3 can be an external source of energy, such as steam, hot water, or other hot fluid, or the effluent from the second reactor.

Other embodiments of the invention will be apparent to those skilled in the art from a consideration of this specification or practice of the invention disclosed herein. It is intended that the specification and example be considered as exemplary only, with the true scope and spirit of the invention being indicated by the following claims.

What is claimed is:

1. A method for making glycol in an adiabatic reactor system, the method comprising:

feeding water and an epoxide into at least one adiabatic reactor under conditions such that epoxide and the

TABLE 2

Summary of Data From Examples 4–13

| Ex. | EO Feed (kg/h) | Water Feed (kg/h) | EG Produced (kg/h) | Catalyst used ($m^3$) | Catalyst Productivity (kg EG/$m^3 \cdot$ h) | EO Conversion (%) | EG Selectivity (%) |
|---|---|---|---|---|---|---|---|
| 4 | 17237 | 137892 | 23970 | 216 | 111 | 99.99 | 98.7 |
| 5 | 17237 | 137892 | 23957 | 344 | 70 | 99.93 | 98.7 |
| 6 | 17237 | 137892 | 23946 | 143 | 167 | 99.98 | 98.6 |
| 7* | 17237 | 137892 | 21497 | n.a. | n.a. | 99.98 | 88.5 |
| 8* | 17237 | 137892 | 21495 | n.a. | n.a. | 99.98 | 88.5 |
| 9 | 17237 | 137892 | 23939 | 133 | 180 | 99.99 | 98.6 |
| 10 | 22680 | 137892 | 31342 | 212 | 148 | 99.95 | 98.1 |
| 11 | 17237 | 137892 | 23292 | 83 | 281 | 99.92 | 96.0 |
| 12 | 17237 | 137892 | 22093 | 83 | 266 | 99.99 | 91.0 |
| 13 | 17237 | 137892 | 23746 | 113 | 210 | 99.97 | 97.8 | n.a. - not applicable
* - comparative example

Examples 4–13 depict desired modes of operating the reactor system during steady state operation (i.e., constant over time). However, there are a number of anticipated events that will lead to unsteady operation, such as start up, fluctuations in feed temperature and composition, and catalyst deactivation. To maintain safe and stable operation of the reactor system under the influence of these factors, it is necessary to be able to manipulate the feed temperature and composition and the reaction rate. The intent of these manipulations is to limit the temperature in the reactors to avoid damaging the catalyst, to extend the useful lifetime of water react to form a glycol product stream, the adiabatic reactor containing an anion exchange resin which undergoes swelling during its useful lifetime, wherein the use of the adiabatic reactor in combination with the anion exchange resin operates to minimize the rate of swelling of the anion exchange resin.

2. The method of claim 1 wherein the catalyst bed in the adiabatic reactor has a height to width ratio of from 0.1:1 to 20:1.

3. The method of claim 1 wherein the rate of catalyst swelling is reduced by at least 10% relative to a non-adiabatic reactor system.

4. The method of claim 1 wherein the catalyst swelling rate is less than 1.0% per day.

5. The method of claim 1 wherein the epoxide is selected from ethylene oxide and propylene oxide and the glycol is selected from ethylene glycol and propylene glycol.

6. The method of claim 1 wherein the diameter of the catalyst bed section of the adiabatic reactor increases from the bottom to the top.

7. A method for making glycol in an adiabatic reactor system, the method comprising:
   a) feeding water and an epoxide into a first adiabatic reactor under conditions such that the epoxide and the water react to form a glycol product stream comprising a glycol and water;
   b) removing the glycol product stream from the first adiabatic reactor and feeding it through at least one external heat exchanger; and
   c) feeding the heat-exchanged glycol product stream through at least one more adiabatic reactor;
   wherein at least one of the adiabatic reactors comprises an anion exchange resin,
   wherein each adiabatic reactor is in series and at least two of the adiabatic reactors are separated by at least one heat exchanger; and
   wherein temperature in the adiabatic reactor system is moderated by cross-exchanging the glycol product stream from at least one of the adiabatic reactors through a heat exchanger with at least one of the water, the epoxide feed, or a glycol product stream from a subsequent adiabatic reactor in series.

8. The method of claim 7 wherein the catalyst bed comprises an anion exchange resin having anions selected from the group consisting of halogen anions, carbonate anions, bicarbonate anions, and combinations thereof.

9. The method of claim 7 wherein, prior to cross-exchanging with the glycol product stream, the temperature of the water or epoxide feed to be cross-exchanged is cool enough to lower the temperature of the glycol product stream so that the temperature of the glycol product stream does not exceed a temperature at which the catalyst bed will significantly degrade.

10. The method of claim 7 wherein the epoxide is selected from ethylene oxide and propylene oxide and the glycol is selected from ethylene glycol and propylene glycol.

11. The method of claim 7 wherein the method is conducted in two adiabatic reactors in series and both adiabatic reactors contain a catalyst bed.

12. The method of claim 7 wherein the method is conducted in two adiabatic reactors in series, and wherein only the second adiabatic reactor in series contains a catalyst bed.

13. The method of claim 12 wherein the glycol product stream from the second adiabatic reactor is cross-exchanged with the glycol product stream from the first adiabatic reactor in a heat exchanger.

14. The method of claim 7 wherein the method is conducted in three adiabatic reactors in series, each adiabatic reactor having at least one heat exchanger located between it and the other adiabatic reactors.

15. The method of claim 7 wherein, in addition to the first adiabatic reactor, water is also fed to at least one more adiabatic reactor.

16. The method of claim 7 wherein, in addition to the first adiabatic reactor, epoxide is also fed to at least one more adiabatic reactor.

17. The method of claim 7 wherein the glycol product stream is fed through at least two heat exchangers prior to being fed to a subsequent adiabatic reactor in series.

* * * * *